United States Patent
Weiss et al.

[11] 4,023,037
[45] May 10, 1977

[54] DECODING COMPOSITE IMAGES OF THREE-DIMENSIONAL OBJECTS BY CONVOLUTION

[75] Inventors: Hermann Weiss, Hamburg; Erhard Klotz, Halstenbek, both of Germany

[73] Assignee: U.S. Philips Corporation, New York, N.Y.

[22] Filed: Mar. 13, 1975

[21] Appl. No.: 558,016

[30] Foreign Application Priority Data

Mar. 25, 1974 Germany .......................... 2414322

[52] U.S. Cl. ............................. 250/313; 250/323; 350/3.5; 350/162 SF
[51] Int. Cl.$^2$ ...................... G03C 9/00; G03H 1/00
[58] Field of Search .......... 350/3.5, 162 R, 162 SF, 350/162 ZP; 250/313, 314, 550, 320–323

[56] References Cited
OTHER PUBLICATIONS

Groh et al., Optics Communications, vol. 1, No. 7, Feb. 1970, pp. 339–340.
Groh et al., Applied Optics, vol. 11, No. 4, Apr. 1972, pp. 931–933.
Wouters et al., Applied Optics, vol. 12, No. 8, Aug. 1973, pp. 1871–1873.
Klotz et al., Optics Communications, vol. 12, No. 2, Oct. 1974, pp. 183–187.

*Primary Examiner*—Ronald J. Stern
*Attorney, Agent, or Firm*—Frank R. Trifari; Simon L. Cohen

[57] ABSTRACT

A method of decoding composite images of three-dimensional objects which are coded by means of a large number of radiation souces of different perspective and which are decoded by means of a point hologram. The point hologram is produced by means of a flat reference beam and by illuminating a shadow mask in the converging beam. The coordinates of the shadow mask correspond to the point image of the source distribution recorded by a hole camera, while the coordinate differences of the holes of the shadow mask have the same value, or a value increased to scale, with respect to the coordinate differences of the point image function of the object plane of the composite image which was nearest to the source distribution during the recording. The decoding of the composite image is effected by shifting between an illumination lens and the point hologram in an incoherent monochromatic converging beam.

6 Claims, 5 Drawing Figures

DECODING COMPOSITE IMAGES OF THREE-DIMENSIONAL OBJECTS BY CONVOLUTION

The invention relates to a method of and a device for the decoding of composite images of three-dimensional objects which are coded by means of a large number of radiation sources of different perspective and which are decoded by means of a point hologram.

It is known that flat objects can be coded by imaging, using incoherent light or X-rays, the object on one and the same film from different positions, so that a composite image is formed. A composite image thus contains information of a three-dimensional object which is projected in one plane. The information concerning the object in this image is not directly accessible; the object can be made visible again only in a second phase, i.e. the decoding of the image. The different recording positions can be mathematically defined by way of a point-like discrete source distribution. Favorable point distributions for the later decoding are either static distributions or so-termed nonredundant distributions such as described by M. J. E. Golay in "Journal of the Optical Society of America", volume 61, page 272.

For the decoding of the composite images, use is made of a mathematical property of these compositions, i.e. the fact that the autocorrelation function thereof approximates in a Dirac's δ-function. The decoding itself is performed in a coherent optical Fourier construction such as described, for example, by G. Groh and G. W. Stroke in Opt. Comm. 1, page 339, 1970. The appearance of the decoded image can be explained in that — when use is made of a non-redundant distribution of $n$ points during the recording of the composite image — the decoding produces an image of an amplitude $n$ which is generated at the area of the central autocorrelation point of the amplitude $n$ and which is surrounded by interfering sub-images of the amplitude 1, caused by the $n(n-1)$ adjacent points of the amplitude 1 in the autocorrelation function. If $n$ is substantially larger than 1, the constructed image appears to be $n$ times brighter than the sub-images which more or less disturb the constructed image.

This optical decoding method has the drawback that the use of the coherent light causes substantial disturbances in the decoded image; these disturbances may amount to the size of an image detail. The elimination of these disturbances which are well known in holography can only be effected, if at all possible, by very slow and prolonged adjusting operations. This drawback makes decoding of three-dimensional objects virtually impossible, because the decoding of the separate faces of the object each time necessitates a different arrangement of the optical construction, so that ever more prolonged adjusting operations are required.

The invention has for its object to provide a method in which these drawbacks are avoided. The method according to the invention is characterized in that a point hologram is produced by means of a flat reference wave and by illuminating a shadow mask in a converging beam, the coordinates of the shadow mask holes corresponding to a point image of a source distribution recorded by a pinhole camera, while the coordinate differences of the holes of the shadow mask have the same value, or a value increased according to scale, in comparison with the coordinate differences of the point image function of an object plane in the composite image which was nearest to the source distribution during recording, the decoding of the composite image being effected by shifting between an illumination lens and the point hologram in an incoherent monochromatic converging beam.

The method is particularly suitable for X-ray imaging in medical diagnostics, i.e. for the imaging of moving three-dimensional objects, such as a beating heart or fast-moving radio-opaque agents injected into blood vessels. The moving object is then simultaneously recorded on a single film by different X-ray tubes from different positions, and following the development of the film the image is decoded in all layers using the method according to the invention. Because of this method of decoding using incoherent light, no adjusting operations are required. Because the separate layers of the object are decoded only by shifting the composite image, the method offers a very fast, smooth progress of the operations.

Embodiments according to the invention will be described in detail hereinafter with reference to the drawing.

The method according to the invention will be described in a simplified manner, taking into account only two recording positions for making the composite image. The possibility of extension to an arbitrary number of perspectives will be readily understood.

Figure 1:
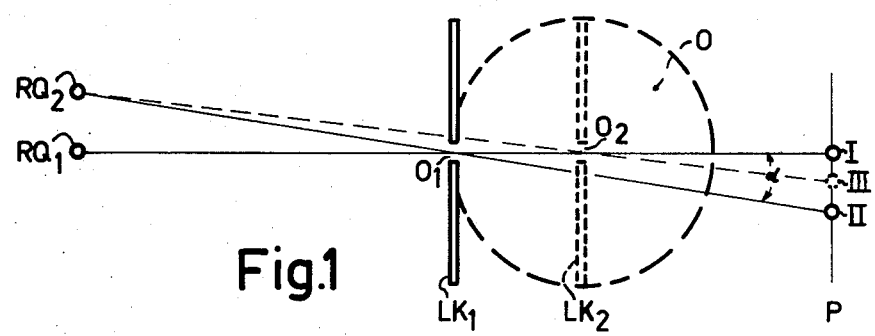
FIG. 1 shows the principle of recording the point image function.

In FIG. 1 a pinhole camera LK1 is used to form a point image of a source distribution, consisting of sources $RQ_1$ and $RQ_2$, formed, for example, by two X-ray tubes, in a plane P. The image of a point $O_1$ realized by the pinhole camera then consists of two points I and II. This point image thus contains information concerning the position of the sources $RQ_1$ and $RQ_2$ relative to the object point $O_1$. If at a later stage a three-dimensional object O is inserted in the projection path instead of the pinhole camera, each point of the object will be imaged in two points, for example, the point $O_2$ in a plane LK2 will be imaged in the points I and III. A double superimposed image of the object is thus obtained. When the object is situated completely behind the location where the pinhole camera was situated during the recording of the point image of the sources, the distance between the image points of an arbitrary object point is always smaller than the distance between the points I and II of the point image function. This will be of importance for the later decoding.

Figure 2:
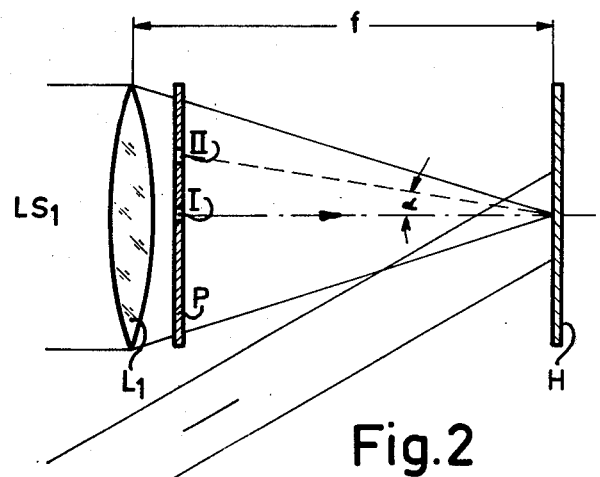
FIG. 2 shows an optical Fourier construction for recording a point hologram.

In FIG. 2 a so-termed point hologram H is recorded on the basis of the point image recording of FIG. 1. A flat coherent light wave $LS_1$, produced by a laser, is focussed by a lens $L_1$ in a focal plane thereof at a focal distance $f$. Behind the lens there is situated a templet P comprising two holes I and II which have the position of the point image formed according to FIG. 1 with respect to each other. Using the reference wave $LS_2$, a hologram H of the point image is then made. In this hologram the information concerning the directions of the points I and II, i.e. concerning the angle α, is stored. However, this only means that the hologram represents a grating having a direction which is modulated by the reference beam. When this holographic grating is brought into the pupil of an imaging system, each image point is doubled, even when incoherent monochromatic light is used. This property of the point hologram is used in FIG. 3 for decoding the composite image recorded from the directions of $RQ_1$ and $RQ_2$ of FIG. 1.

Figure 3:
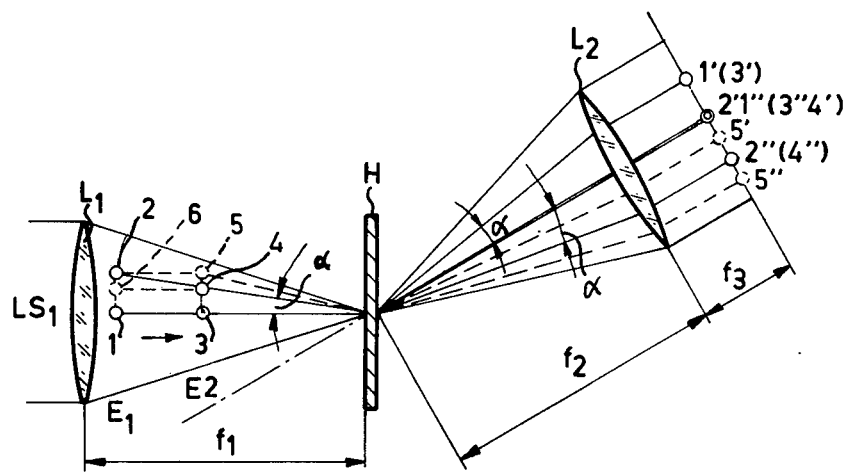
FIG. 3 shows a device for decoding a composite image.

FIG. 3 shows a construction similar to that of FIG. 2; the hologram H remains at the recording location; instead of the point distribution P of FIG. 2, the composite image is now brought into a plane $E_1$. This image is illuminated by an incoherent monochromatic light beam $LS_1$ converged by the lens $L_1$. The light source 1 may be a monochromatic thermal light source such as a mercury vapor lamp or a laser together with a device for effecting static direction variations in the beam. First the imaging of two points 1 and 2 in the plane $E_1$ by the hologram H and a second lens $L_2$ will be described. The distances $f_1$, $f_2$ and $F_3$ are focal distances of the successive lenses. The points 1 and 2 enclose, in conjunction with the center of the hologram, the angle α of FIG. 2. The projection beam, starting from point 1, coincides with the optical axis and is deflected by the hologram H, situated in the projection pupil, in the direction of the reference beam used for recording the hologram, and the projection beam is at the same time doubled by the angle α. The lens $L_2$ then produces two image points 1" and 1'; the $O^{st}$ and the $1^{st}$ order of the hologram are of no importance. Accordingly, the projection of the point 2 produces the images 2' and 2". The image points 1" amd 2' are then superimposed because of the fact that the points 1 and 2 are formed at the angle α and the fact that the splitting of each separate ray in the recording of the hologram in FIG. 2 is effected at the angle α. However, this means that all points 1 and 2 of the composite image, arising from a point in the plane of the hole camera $LK_1$ in FIG. 1 — because all points of the plane in which the point $O_1$ is situated were doubled by the same distance — are imaged in the three points 1', 2" and the point 2', 1". The latter point then has a double intensity with respect to the neighbouring points 1' and 2". However, this is exactly the described autocorrelation of the source distribution. The point 2' 1" is a constructive point of the decoded composite image; the points 1' and 2" are neighbouring points which disturb the constructive image. Obviously, the same considerations are applicable to all points of the object in the plane of the point $O_1$ in FIG. 1. When the object is not recorded from two directions only, but from n directions, the intensity of the constructive image point is, consequently, increased n times in comparison with the neighbouring points, provided that at least no neighbouring image points are constructively superimposed. However, the latter is precluded if the said nonredundant point distribution is used as source distributions.

The decoding of all other object layers is then effected by shifting the composite image in the direction of the hologram H. When the composite image is situated in a plane $E_2$, points 3 and 4 which are then visible at the angle α are constructively superimposed with respect to a double point 4'3", at the same time the neighbouring points 3' and 4" being formed. This means that now each time all points of the composite image which are situated at a smaller distance from the points 3 and 4 are constructively projected, i.e. the points of the original object, which are situated in the plane of point $L_2$ of FIG. 1. However, all points having other distances, for example, the points 3 and 5, are no longer constructively superimposed. Conversely, points such as the points 1 and 6 of the composite image are not constructively superimposed in position $E_1$. The shifting of the composite image from the plane $E_1$ to the plane $E_2$ thus provides adaptation of corresponding object planes to the hologram H; this is feasible because of the converging beam path in FIG. 3.

If the blurred recording of a moving object is considered as a number of superimposed clear images at different planes in space the use of the above described method wherein one of a number of recorded planes may be separately received, the recording of a number of clear images of a moving object may be accomplished in the exact same manner as the recording and viewing of a stationary three-dimensional object.

Figure 4:
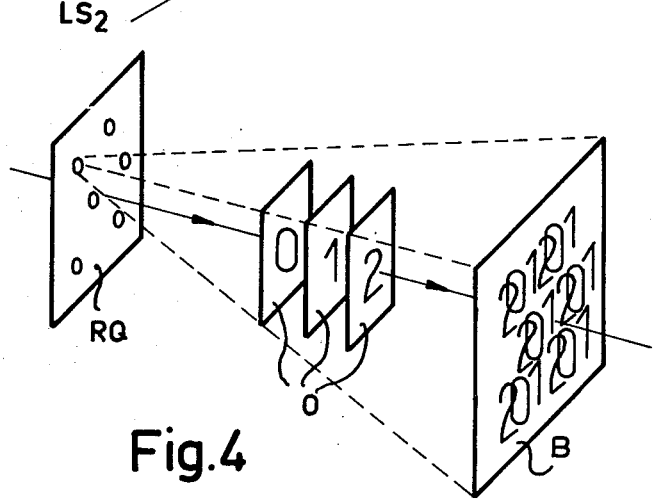
FIG. 4 shows the multiple projection of a three-dimensional object.

FIG. 4 shows the extension of the recording principle with a plurality of sources RQ and planes O, 1, 2 of the object O. The reference B represents the composite image of the digits.

Figure 5:
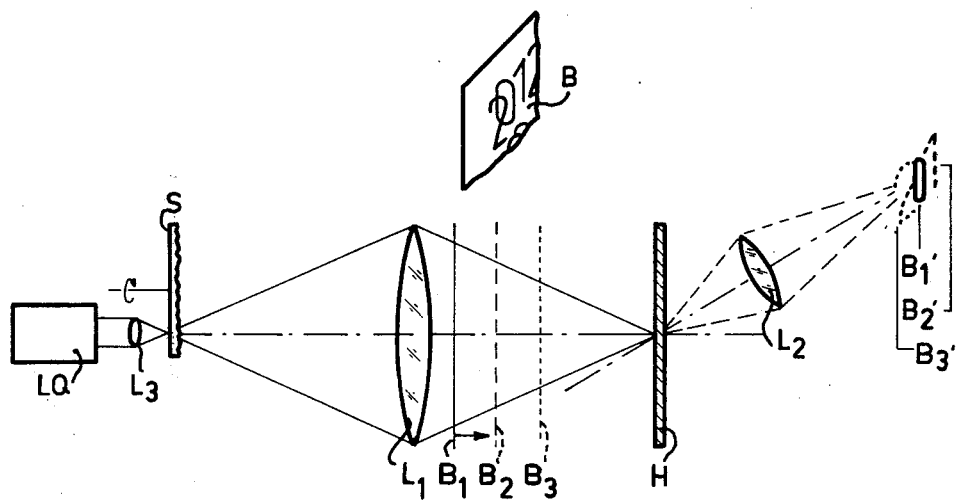
FIG. 5 illustrates the incoherent decoding method.

FIG. 5 shows an example of an incoherent decoding of the composite image. A lens $L_3$ produces a diverging light beam of a laser LQ. In This diverging beam there is arranged a rotating ground glass screen S which disturbs or substantially reduces the spatial coherence of the laser light. The lens $L_1$ then illuminates in the converging beam the composite image which is shifted in the positions $B_1$, $B_2$, $B_3$. By means of the point hologram H and the lens $L_2$, the decoded images $B_1'$, $B_2'$, $B_3'$ of the three-dimensional object are successively produced in the image plane. These images do not contain any coherent interference.

What is claimed is:

1. A method of encoding and decoding composite images of three-dimensional objects comprising recording a three dimensional object with radiation from a large number of radiation sources of different perspective, exposing a holographic recording medium to a coherent reference wave having a plane wave front and simultaneously illuminating with a converging coherent beam a shadow mask provided with holes having coordinates corresponding to an image of the distribution of said radiation sources recorded by a pinhole camera and exposing said holographic recording medium to the radiation passing through said shadow mask thereby producing a coded point hologram, illuminating the coded point hologram with a converging beam of incoherent monochromatic radiation through the recording of said object, shifting the recording of said object with respect to the point hologram in said incoherent monochromatic converging beam, and imaging the radiation passing through said decoded hologram.

2. A method as claimed in claim 1, wherein the step of illuminating the coded point hologram comprises rotating a ground glass screen in a diverging laser beam.

3. A method as claimed in claim 1, wherein the step of illuminating the coded point hologram comprises illuminating said hologram with a monochromatic thermal light source.

4. A method as claimed in claim 1, wherein the step of recording said three dimensional object comprises exposing a film to X-ray sources and developing the film.

5. A device for encoding and decoding composite images of three dimensional objects, comprising a plurality of sources of incoherent radiation, a radiation-sensitive recording medium in the path of the light from said incoherent sources, said three dimensional object being positioned between said sources and said recording medium in the path of the light from the sources, thereby providing an encoded image of the object, a source of converging coherent rediation, a holographic recording medium in the path of said converging coherent radiation, a planar coherent reference wave illuminating said holographic recording medium in the vicinity of said converging coherent radiation, a shadow mask having an aperture distribution corresponding to the distribution of incoherent sources and being positioned in the path of said converging radiation, whereby a decoding hologram is formed, a source of converging incoherent radiation, said encoded recording of said object being placed in the path of said converging incoherent radiation, said decoding hologram being placed at the focal point of said converging incoherent radiation, and means for imaging the radiation passing through said decoding hologram.

6. A device as claimed in claim 5, wherein said source of converging incoherent radiation comprises a laser, a rotating ground glass screen in the path of the radiation from said laser, and a converging lens in the path of the radiation passing through said rotating ground glass screen.

* * * * *